United States Patent
Henkelmann et al.

(10) Patent No.: US 6,504,064 B1
(45) Date of Patent: Jan. 7, 2003

(54) PREPARATION OF ENOL ETHERS

(75) Inventors: Jochem Henkelmann, Mannheim (DE); Heike Becker, Frankenthal (DE); Juan Aiscar, Mannheim (DE); Boris A. Trofimov, Irkutsk (RU); Nina K. Gusarova, Irkutsk (RU); Ludmilla A. Oparina, Irkutsk (RU);

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/884,969

(22) Filed: Jun. 21, 2001

(30) Foreign Application Priority Data

Jun. 29, 2000 (DE) .......................................... 100 31 755

(51) Int. Cl.⁷ .......................... C07C 41/06; C07C 41/09
(52) U.S. Cl. ........................................ 568/688; 568/689
(58) Field of Search .................................. 568/688, 689

(56) References Cited

U.S. PATENT DOCUMENTS

| | | | | |
|---|---|---|---|---|
| 2,969,395 A | * | 1/1961 | Nedwick et al. .............. | 203/77 |
| 3,213,155 A | * | 10/1965 | Schriesheim et al. ....... | 208/189 |
| 5,767,325 A | | 6/1998 | Schroeder ................... | 568/691 |
| 6,060,035 A | | 5/2000 | Teles .......................... | 423/326 |
| 6,087,538 A | | 7/2000 | Teles .......................... | 568/591 |
| 6,120,744 A | | 9/2000 | Teles .......................... | 423/99 |

FOREIGN PATENT DOCUMENTS

| | | | |
|---|---|---|---|
| DE | 199 24 050 A1 | * | 11/2000 |
| DE | 199 24 159 A1 | * | 11/2000 |
| EP | 887 330 | | 12/1988 |
| EP | 887 332 | | 12/1988 |
| EP | 776 879 | | 6/1997 |
| EP | 887 331 | | 12/1998 |
| SU | 263 890 | | 1/1989 |
| SU | 265 289 | | 3/1989 |
| SU | 267 629 | | 5/1989 |
| WO | 98/58894 | | 12/1998 |

OTHER PUBLICATIONS

Bretherick's Handbook of Reactive Chemical Hazards, 5th Ed., Edited by PG Urben.
Russian Journal of Org. Chem. vol. 31, No. 9, 1995, pp 1233–1252, Trofimov.
Ullmann's Enc. of Ind.Chem.6thEd., 1999, Reaction of Acetylene with Alcohols.

* cited by examiner

*Primary Examiner*—Rosalynd Keys
(74) *Attorney, Agent, or Firm*—Keil & Weinkauf

(57) ABSTRACT

Enol ethers of the formula (I)

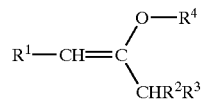

where $R^1$ to $R^3$ are each, independently of one another, hydrogen or a carbon-containing organic radical and $R^4$ is an unsubstituted or substituted alkyl radical, are prepared by reacting alcohols of the formula (II)

$R^4$—OH  (II), with alkynes of the formula (IIIa), alkadienes of the formula (IIIb)

$R^1$—C≡C—CHR²R³  (IIIa), $R^1$—CH=C=CR²R³  (IIIb)

or mixtures thereof, where $R^1$ to $R^4$ are as defined above, in the presence of an alkali metal alkoxide and a polar, aprotic solvent.

10 Claims, No Drawings

PREPARATION OF ENOL ETHERS

The present invention relates to a process for preparing enol ethers of the formula (I)

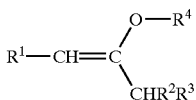
(I)

where $R^1$ to $R^3$ are each, independently of one another, hydrogen or a carbon-containing organic radical and $R^4$ is an unsubstituted or substituted alkyl radical, by reacting alcohols of the formula (II)

$$R^4\text{—OH} \tag{II}$$

with alkynes of the formula (IIIa), alkadienes of the formula (IIIb)

$$R^1\text{—C}\equiv\text{C—CHR}^2R^3 \tag{IIIa}$$

$$R^1\text{—CH}=\text{C}=\text{CR}^2R^3 \tag{IIIb}$$

or mixtures thereof, where $R^1$ to $R^4$ are as defined above.

Enol ethers are important intermediates in the synthesis of many chemical products, in particular pharmaceuticals, agrochemicals and cosmetics. Furthermore, enol ethers are important monomeric building blocks in the preparation of polymers.

Enol ethers are generally prepared by alkenylation of alcohols in the presence of basic catalysts. The ethenylation of alcohols is usually carried out under superatmospheric pressure, e.g. 1.6 MPa in the case of methyl vinyl ether, and high temperatures in the range from 120 to 180° C. (cf. Ullmann's Encyclopedia of Industrial Chemistry, 6$^{th}$ edition, 1999 Electronic Release, Chapter "VINYL ETHERS").

B. A. Trofimov, Russian Journal of Organic Chemistry, Vol. 31, 1995, pages 1233 to 1252, describes the reaction of alcohols with ethyne under atmospheric pressure and at from 20 to 100° C. in the presence of a superbasic catalyst system comprising potassium hydroxide in dimethyl sulfoxide (DMSO).

If alkenylations are carried out using propyne or higher molecular weight alkynes, the reaction conditions are generally more drastic. DD 263 890 A3 describes the preparation of alkoxypropenes from propyne and alcohols at from 190 to 240° C. and a pressure of from 41 to 62 atm in the presence of potassium hydroxide in the liquid phase. Disadvantages are the relatively severe reaction conditions in respect of temperature and pressure.

High temperature and high pressure represent a safety risk when handling alkynes and alkenes. Thus, according to L. Bretherick et al., "Bretherick's Handbook of Reactive Chemical Hazards", 5$^{th}$ edition, Butterworth-Heinemann, Oxford 1995, pages 5410 to 5411, decomposition of propyne in the gas phase at 20° C. can occur at as low as 0.35 MPa abs and decomposition of 1,2-propadiene in the gas phase at 25° C. can occur at as low as 0.2 MPa abs.

DD 267 629 A3 and DD 265 289 A3 describe the alkenylation of methanol and ethanol using propene over heterogeneous zinc-containing catalysts in the gas phase at from atmospheric pressure to 10 atm and at from 250 to 300° C. A disadvantage is the very high temperature required in this process.

EP 0 887 331 A1 and EP 0 887 332 A1 disclose the preparation of enol ethers by reaction of alcohols with alkynes in the gas phase in the presence of an X-ray-amorphous zinc or cadmium silicate. The preparation of 2-methoxypropene at 170° C. and a pressure of 1.2 bar abs is described. In this process, too, a high temperature is necessary for the reaction.

Owing to the disadvantages of the alkenylation processes mentioned, 2-methoxypropene, for example, is generally obtained by dissociation of the corresponding ketal in the gas phase over various heterogeneous catalysts. Appropriate methods are described, for example, in WO 98/58894, EP 0 887 330 A1 and EP 0 776 879 A1. Disadvantages of this synthetic route are the unfavorable starting material basis, namely the corresponding ketones, and the multistep nature of the process chain, which comprises ketalization of the ketones and subsequent dissociation of the ketals.

It is an object of the present invention to find a process for preparing enol ethers of the propene group and higher molecular weight alkene groups, which no longer has the abovementioned disadvantages, is based on economical, readily available raw materials and, in particular, makes possible a high yield of enol ether in only one synthesis step under mild reaction conditions. We have found that this object is achieved by a process for preparing enol ethers of the formula (I)

(I)

where $R^1$ to $R^3$ are each, independently of one another, hydrogen or a carbon-containing organic radical and $R^4$ is an unsubstituted or substituted alkyl radical, by reacting alcohols of the formula (II)

$$R^4\text{—OH} \tag{II}$$

with alkynes of the formula (IIIa), alkadienes of the formula (IIIb)

$$R^1\text{—C}\equiv\text{C—CHR}^2R^3 \tag{IIIa}$$

$$R^1\text{—CH}=\text{C}=\text{CR}^2R^3 \tag{IIIb}$$

or mixtures thereof, where $R^1$ to $R^4$ are as defined above, wherein the reaction is carried out in the presence of an alkali metal alkoxide and a polar, aprotic solvent.

Alkali metal alkoxides which can be used in the process of the present invention are in principle all aliphatic, araliphatic, saturated, noncyclic or cyclic alkoxides of lithium, sodium, potassium, rubidium or cesium. Examples which may be mentioned are alkali metal methoxides, alkali metal ethoxides, alkali metal 1-propoxides (alkali metal propoxides), alkali metal 2-propoxides (alkali metal isopropoxides), alkali metal 1-butoxides (alkali metal butoxides), alkali metal 2-butoxides (alkali metal sec-butoxides), alkali metal 2-methyl-1-propoxides (alkali metal isobutoxides), alkali metal 1,1-dimethyl-1-ethoxides (alkali metal tert-butoxides), alkali metal 1-pentoxides, alkali metal 2-pentoxides, alkali metal 3-pentoxides, alkali metal 2-methyl-1-butoxides, alkali metal 3-methyl-1-butoxides (alkali metal isoamylates), alkali metal 3-methyl-2-butoxides, alkali metal 2,2-dimethyl-1-propoxides, alkali metal 2-methyl-2-butoxides (alkali metal tert-amylates), alkali metal cyclopentoxides, alkali metal cyclohexoxides, alkali metal benzylates, alkali metal 2-phenyl-1-ethoxides, alkali metal 2-phenyl-2-propoxides or mixtures thereof, where alkali metal may be lithium, sodium, potassium, rubidium or cesium.

Preference is given to using the tertiary alkali metal alkoxides, for example sodium tert-butoxide, potassium tert-butoxide, cesium tert-butoxide, sodium tert-amylate, potassium tert-amylate, cesium tert-amylate or mixtures thereof. Particular preference is given to using potassium tert-butoxide.

The alkali metal alkoxides can also be used in combination with alkali metal hydroxides, for example sodium hydroxide, potassium hydroxide or cesium hydroxide, and/or alkali metal halides, preferably fluorides such as sodium fluoride, potassium fluoride or cesium fluoride. If the alkali metal alkoxides are used in combination with further alkali metal compounds, the combination with cesium fluoride is preferred.

In the process of the present invention, the alkali metal alkoxide is generally used in an amount of from 1 to 50 mol %, based on the alcohol (II) used. Preference is given to an amount of from 5 to 30 mol %, particularly preferably from 10 to 20 mol %.

The alkali metal alkoxides used according to the present invention are mostly commercially available, but can, if necessary, be prepared by known methods. Suitable methods are, for example, reaction of the corresponding alcohols with (i) elemental alkali metals, (ii) with alkali metal hydroxides and removal of the water of reaction formed and (iii) with other alkoxides and removal of the other alcohols formed.

Furthermore, the presence of a polar, aprotic solvent is essential in the process of the present invention. Suitable polar, aprotic solvents are liquid under the reaction conditions and preferably also at room temperature. Examples which may be mentioned are tetrahydrofuran, 1,4-dioxane, N-methylpyrrolidone, N-methylpiperidone, dimethyl sulfoxide, glycol ethers (e.g. 1,2-dimethoxyethane or bis(2-methoxyethyl) ether), dimethylformamide, dimethylformanilide or mixtures thereof. Particular preference is given to using N-methylpyrrolidone.

The polar, aprotic solvent can also be used in admixture with further aprotic solvents, for example saturated aliphatic or aromatic compounds. Examples which may be mentioned are alkanes such as hexanes, heptanes, octanes, nonanes, decanes or petroleum spirit, and aromatic compounds such as toluene or xylenes. The polar, aprotic solvents are preferably used in the absence of further polar solvents.

The amount of polar, aprotic solvent is generally chosen so that at least one equivalent of the alkyne (IIIa) or the alkadiene (IIIb) or the mixture thereof, based on the alcohol (II) used, dissolves under the reaction conditions and can easily be determined for each reaction system by simple experiments.

The process of the present invention is very particularly preferably carried out in the presence of potassium tert-butoxide and N-methylpyrrolidone.

The process of the present invention is generally carried out at from 80 to 150° C., preferably from 100 to 130° C. and particularly preferably from 110 to 130° C., and at from 0.1 to 2.5 MPa abs, preferably from 0.1 to 1.0 MPa abs, in particular from 0.10 to 0.14 MPa abs.

The enol ethers which can be prepared in the process of the present invention have the formula (I)

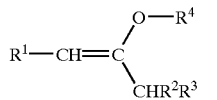
(I)

where $R^1$ to $R^3$ are each, independently of one another, hydrogen or a carbon-containing organic radical and $R^4$ is an unsubstituted or substituted alkyl radical.

For the purposes of the present invention, a carbon-containing organic radical is an unsubstituted or substituted, aliphatic, aromatic or araliphatic radical having from 1 to 12 carbon atoms. This radical can contain one or more heteroatoms such as oxygen, nitrogen or sulfur, for example —O—, —S—, —NR—, —CO— and/or —N= in aliphatic or aromatic systems, and/or be substituted by one or more functional groups containing, for example, oxygen, nitrogen, sulfur and/or halogen, for example by fluorine, chlorine, bromine, iodine and/or a cyano group. Preferred examples of carbon-containing organic radicals are $C_1$–$C_{10}$-alkyl, particularly preferably $C_1$–$C_6$-alkyl, $C_6$–$C_{10}$-aryl, particularly preferably phenyl, $C_7$–$C_{10}$-aralkyl, particularly preferably phenylmethyl, and $C_7$–$C_{10}$-alkaryl, particularly preferably 2-methylphenyl, 3-methylphenyl and 4-methylphenyl.

For the purposes of the present invention, an unsubstituted or substituted alkyl radical is an alkyl radical having a total of from 1 to 12 carbon atoms which may be substituted by one or more functional groups containing, for example, oxygen, nitrogen, sulfur and/or halogen, for example by fluorine, chlorine, bromine, iodine and/or a cyano group. Preferred examples of unsubstituted or substituted alkyl radicals are $C_1$–$C_{10}$-alkyl, particularly preferably $C_1$–$C_6$-alkyl, and $C_7$–$C_{10}$-aralkyl, particularly preferably phenylmethyl.

The process of the present invention is very particularly preferably employed for preparing enol ethers (I) in which the radical $R^4$ is a $C_1$–$C_4$-alkyl radical, for example methyl, ethyl, 1-propyl, 2-propyl, 1-butyl, 2-butyl, 2-methyl-1-propyl or 2-methyl-2-propyl, in particular methyl.

Furthermore, the process of the present invention is very particularly preferably employed for preparing enol ethers (I) in which the radicals $R^1$ to $R^3$ are each, independently of one another, hydrogen, or a $C_1$–$C_4$-alkyl radical, for example methyl, ethyl, 1-propyl, 2-propyl, 1-butyl, 2-butyl, 2-methyl-1-propyl or 2-methyl-2-propyl, in particular hydrogen.

Examples of enol ethers (I) which are very particularly preferably prepared by the process of the present invention are 2-methoxypropene, 2-ethoxypropene, 2-propoxypropene, 2-(sec-propoxy)propene, 2-butoxypropene, 2-(sec-butoxy)propene, 2-(isobutoxy)propene, 2-(tert-butoxy)propene, 2-methoxy-1-butene, 2-ethoxy-1-butene, 2-propoxy-1-butene, 2-(sec-propoxy)-1-butene, 2-butoxy-1-butene, 2-(sec-butoxy)-1-butene, 2-(isobutoxy)-1-butene, 2-(tert-butoxy)-1-butene, 2-methoxy-2-butene, 2-ethoxy-2-butene, 2-propoxy-2-butene, 2-(sec-propoxy)-2-butene, 2-butoxy-2-butene, 2-(sec-butoxy)-2-butene, 2-(isobutoxy)-2-butene and 2-(tert-butoxy)-2-butene, in particular 2-methoxypropene.

The alcohols to be used have the formula (II)

where $R^4$ is as defined above. Depending on the radical $R^4$ and the reaction conditions, the alcohols, in each case considered as the pure substance, can be present in gaseous, liquid or solid form.

If the alcohols are in gaseous form under the specified conditions, they are nevertheless generally added in liquid form at a temperature below their boiling point to the heated reaction mixture, although introduction as a gas is also possible. If the alcohols are liquid under the specified conditions, they are generally also added in liquid form. If the alcohols are solid under the specified conditions, they are generally dissolved in the polar, aprotic solvent.

The alkynes to be used have the formula (IIIa), and the alkadienes to be used have the formula (IIIb)

$$R^1{-}C{\equiv}C{-}CHR^2R^3 \quad \text{(IIIa)},$$

$$R^1{-}CH{=}C{=}CR^2R^3 \quad \text{(IIIb)}$$

where the radicals $R^1$ to $R^3$ are, independently of one another, as defined above.

If the alkynes and/or alkadienes are gaseous or liquid, they are generally also added in this state. If the alkynes and/or alkadienes are solid, they are generally dissolved in the polar aprotic solvent and added as solution. To reduce the reaction rate at the point of introduction and thus also the formation of by-products, it may be advantageous in the case of liquid alkynes and/or alkadienes to dissolve them beforehand in the polar aprotic solvent and to introduce them in diluted form.

The alkynes (IIIa), alkadienes (IIIb) and their mixtures can, in the process of the present invention, further comprise other compounds such as saturated or unsaturated hydrocarbons or inert gases such as nitrogen or noble gases.

Under the reaction conditions employed according to the present invention, both the alkynes (IIIa) and the alkadienes (IIIb) are converted into the enol ethers (I). Thus, inexpensive feedstock streams which are readily available in industry can also be used particularly advantageously. For example, 2-alkoxypropenes can be prepared from a mixture comprising propyne and 1,2-propadiene. Furthermore, 2-alkoxybutenes can be prepared from a mixture comprising 1-butyne, 2-butyne and 1,2-butadiene.

In a preferred embodiment for preparing 2-methoxypropene, a gas mixture comprising propyne and 1,2-propadiene is used as feedstock. The molar ratio of propyne to 1,2-propadiene can vary within a wide range and is generally from infinity (i.e. absence of 1,2-propadiene) to two. This mixture can come, for example, from the work-up of a $C_3$ stream from a steam cracker and may further comprise propane as additional component.

The molar ratio of the alcohol (II) to the alkyne (IIIa) or the alkadiene (IIIb) or the mixture thereof is generally from 1:1 to 1:2, preferably from 1:1 to 1:1.3.

The process of the present invention can be carried out batchwise, semicontinuously or continuously. When the reaction is carried out continuously, substances and compounds which react with the alkali metal alkoxide (e.g. water), which lead to an explosive risk (e.g. oxygen) and which lead to undesirable by-products (e.g. ketones, aldehydes, esters, acids, acid chlorides or acid anhydrides) should be substantially excluded.

In a general embodiment for carrying the process out batchwise, the polar, aprotic solvent, the alkaline metal alkoxide, the alcohol (II) and the alkyne (IIIa) or the alkadiene (IIIb) or the mixture thereof are combined, mixed and brought to the reaction conditions. After the reaction is complete, the reaction mixture is passed to work-up, preferably by distillation, and the desired enol ether (I) is isolated. It may be possible and useful to separate off and isolate at least part of the enol ether (I) formed by vaporization during the reaction.

In a general embodiment for carrying out the process semicontinuously, the polar, aprotic solvent, the alkaline metal alkoxide and the alcohol (II) are placed in a reaction vessel, mixed and brought to the reaction temperature. The alkyne (IIIa) or the alkadiene (IIIb) or the mixture thereof is then fed in continuously until the desired amount has been reached. It can be introduced in gaseous or liquid form. When it is added in liquid form, it is possible to use pure, liquid alkyne (IIIa), pure, liquid alkadiene (IIIb) or a mixture of the two or else a mixture of these components in a solvent, preferably the polar, aprotic solvent. When the addition of alkyne (IIIa) and/or alkadiene (IIIb) is complete, the reaction mixture can be left under the reaction conditions for a further time. After the reaction is complete, the reaction mixture is passed on to work-up, preferably by distillation, and the desired enol ether (I) is isolated. It may be possible and useful to separate off and isolate at least part of the enol ether (I) formed by vaporization during the reaction.

In a general embodiment for carrying out the process continuously, the polar, aprotic solvent and the alkali metal alkoxide are placed in a reaction vessel and brought to the reaction temperature. The alcohol (II) and the alkyne (IIIa), alkadiene (IIIb) or mixture thereof are then metered in continuously in the desired ratio. In general, the alcohol (II) is added in liquid form, if necessary dissolved in a solvent, preferably the polar, aprotic solvent. The alkyne (IIIa) and/or the alkadiene (IIIb) can be introduced in gaseous or liquid form. When it is added in liquid form, it is possible to use pure, liquid alkyne (IIIa), pure, liquid alkadiene (IIIb) or a mixture of the two or else a mixture of these components in a solvent, preferably the polar, aprotic solvent. In a variant (a) of the continuous procedure, the enol ether (I) formed is continuously taken from the reaction vessel by means of vaporization and isolated. This is possible when the enol ether is readily vaporizable under the reaction conditions. Any alcohol or alkyne vaporized is/are returned to the reaction vessel. In another variant (b), liquid reaction mixture is taken off continuously and the enol ether (I) formed is isolated in a downstream stage, for example by distillation or extraction. Relatively high-boiling by-products may also be separated off. The remaining mixture, which comprises mainly the polar, aprotic solvent and the alkali metal alkoxide, is returned to the reaction vessel.

In a preferred embodiment for preparing 2-methoxypropene, N-methylpyrrolidone, potassium tert-butoxide and methanol are placed in a reaction vessel and mixed. The molar ratio of potassium tert-butoxide to methanol is preferably in the range from 1:5 to 1:10. After heating to the desired reaction temperature, which is preferably in the range from 110 to 130° C., a gas mixture comprising propyne and 1,2-propadiene is passed in continuously under atmospheric pressure. The 2-methoxypropene formed is readily volatile under the reaction conditions and is therefore continuously vaporized from the reaction mixture and is condensed in a cold trap. The entrained $C_3$-hydrocarbons can be at least partly recirculated. The remaining part of the $C_3$-hydrocarbons is discharged as a purge stream. After the desired amount of propyne- and 1,2-propadiene-containing gas mixture has been fed in, introduction of gas is stopped and the reaction system is left for a short time under the reaction conditions to allow an after-reaction and to vaporize more of the 2-methoxypropene formed. Distillation of the reaction mixture condensed in the cold trap enables 2-methoxypropene to be obtained in high purity and high yield.

The process of the present invention makes it possible to prepare enol ethers of the propene radical and of relatively high molecular weight alkene radicals using the generally readily available, economical and inexpensive starting materials alcohol and alkyne under very mild reaction conditions, i.e. at low temperature and low pressure, in only one synthesis step to give a high yield and a high purity.

The very mild reaction conditions make a particularly economical and safe synthesis possible. The risk of decomposition of the gaseous alkynes has been able to be minimized under these conditions. In addition, the plant can be constructed for lower temperatures and pressures.

In the case of the preferred use of N-methylpyrrolidone as polar, aprotic solvent, there are further advantages compared to dimethyl sulfoxide, which has previously been described, for example, as solvent for the ethynylation of alcohols in the presence of a superbasic catalyst system, in terms of a lower tendency to decompose, easier removal from the reaction system and lower starting material costs.

EXAMPLES

Example 1

In a reaction vessel, 50 ml of N-methylpyrrolidone were mixed with 3.2 g (100 mmol) of methanol and 11 g (50 mmol) of cesium tert-amylate. The mixture was heated to 100° C. while stirring, and 1 standard 1/h of a 9:1 mixture of propyne and 1,2-propadiene was passed in under atmospheric pressure for 2 hours. The temperature was subsequently increased to 120° C. and, while continuously passing in further propyne/1,2-propadiene mixture in an amount of 1 standard 1/h for 10 hours, a mixture of 2 ml of N-methylpyrrolidone and 1.6 g (50 mmol) of methanol was slowly added dropwise. During this operation, 10.9 g of condensate consisting of 9.4 g (130 mmol) of 2-methoxypropene, 0.3 g (9 mmol) of methanol and 1.2 g of propyne/1,2-propadiene were collected in a downstream cold trap.

The remaining reaction mixture was left for another 10 hours at 120° C., with a propyne/1,2-propadiene mixture continuing to be passed in continuously in an amount of 1 standard 1/h and a further 4.8 g (150 mmol) of methanol slowly being added dropwise. A further 7.2 g of condensate comprising 3.9 g (54 mmol) of 2-methoxypropene, 2.2 g (69 mmol) of methanol and 0.9 g of propyne/1,2-propadiene were collected. The remaining reaction mixture comprised 1.0 g (31 mmol) of methanol.

The total yield of 2-methoxypropene, based on methanol, was thus 61%. The conversion of methanol was 64%.

Example 2

In a reaction vessel, 50 ml of N-methylpyrrolidone were mixed with 3.2 g (100 mmol) of methanol and 2.8 g (25 mmol) of potassium tert-butoxide. The mixture was heated while stirring and, at 120° C., 1 standard 1/h of a 9:1 mixture of propyne and 1,2-propadiene was passed in under atmospheric pressure for 8 hours. 7.2 g of condensate consisting of 5.4 g (75 mmol) of 2-methoxyptopene, 0.6 g (19 mmol) of methanol and 1.2 g of propyne/1,2-propadiene were collected in a downstream cold trap.

The remaining reaction mixture was left at 120° C. for a further 4 hours, during which time further propyne/1,2-propadiene mixture was passed in continuously in an amount of 1 standard 1/h and a further 1.6 g (50 mmol) of methanol were slowly added dropwise. The condensate collected comprised 3.8 g (53 mmol) of 2-methoxypropene, 0.04 g (1 mmol) of methanol and 0.5 g of propyne/1,2-propadiene.

The total yield of 2-methoxypropene, based on methanol, was 85%. The conversion of methanol was 87%.

Example 3

500 ml of N-methylpyrrolidone and 56.1 g (0.5 mol) of potassium tert-butoxide were placed in a reaction vessel and mixed. The mixture was heated while stirring and, at 120° C. under atmospheric pressure, a total of 64.1 g (2.0 mol) of methanol at a metering rate of 10 ml/h and a 3:2 mixture of propyne and 1,2-propadiene at a metering rate of 11 standard 1/h were introduced continuously. The methanol/2-methoxypropene azeotrope formed was collected continuously in a condenser operated at −5° C. and returned to the reaction vessel. After 4 hours, the condensate consisted exclusively of 2-methoxypropene. Over the total reaction time of 8 hours, a total of 85.7 g (1.19 mol) of 2-methoxypropene were isolated after purification by distillation. This corresponds to a yield of 60%, based on the methanol used.

A total of 32 g (1.0 mol) of methanol and 44.8 standard 1 of a 3:2 mixture of propyne and 1,2-propadiene were added continuously to the remaining mixture in the reaction vessel over a further period of 6 hours. After the condensate had been returned five times, 33.8 g (0.47 mol) of 2-methoxypropene were obtained. This corresponds to a further yield of 47%, based on the methanol used.

We claim:

1. A process for preparing enol ethers of formula (I)

where $R^1$ to $R^3$ are each, independently of one another, hydrogen or a carbon-containing organic radical and $R^4$ is an unsubstituted or substituted alkyl radical, by reacting alcohols of formula (II)

$$R^4\text{—OH} \tag{II}$$

with a mixture of alkynes of formula (IIIa) and alkadienes of formula (IIIb)

where $R^1$ to $R^4$ are as defined above, wherein the reaction is carried out in the presence of an alkali metal alkoxide and a polar, aprotic solvent.

2. A process as claimed in claim 1, wherein enol ethers (I) in which $R^4$ is a $C_1$–$C_4$-alkyl radical are prepared.

3. A process as claimed in claim 1, wherein enol ethers (I) in which $R^1$ to $R^3$ are each, independently of one another, hydrogen or a $C_1$–$C_4$-alkyl radical are prepared.

4. A process as claimed in claim 1, wherein the alkali metal alkoxide is used in an amount of from 1 to 50 mol %, based on the alcohol (II) used.

5. A process as claimed in claim 1, wherein the alkali metal alkoxide used is a tertiary alkali metal alkoxide.

6. A process as claimed in claim 1, wherein the alkali metal alkoxide used is potassium tert-butoxide.

7. A process as claimed in claim 1, wherein the polar, aprotic solvent used is N-methylpyrrolidone.

8. A process as claimed in claim 1, wherein the reaction is carried out at from 80 to 150° C. and a pressure of from 0.1 to 2.5 MPa abs.

9. A process as claimed in claim 1, wherein 2-methoxypropene is prepared as enol ether (I).

10. A process as claimed in claim 9, wherein a mixture comprising propyne and 1,2-propadiene is used as starting material.

* * * * *